US00PP27914P2

(12) United States Plant Patent
Unger

(10) Patent No.: US PP27,914 P2
(45) Date of Patent: Apr. 18, 2017

(54) ***HELICHRYSUM* PLANT NAMED 'WESHECHRSISTI'**

(50) Latin Name: *Helichrysum petiolare*
Varietal Denomination: Weshechrsisti

(71) Applicant: Christian Unger, Worms (DE)

(72) Inventor: Christian Unger, Worms (DE)

(73) Assignee: Gartenbau and Spezialkulturn Westhoff GbR, Sudlohn (DE)

( * ) Notice: Subject to any disclaimer, the term of this patent is extended or adjusted under 35 U.S.C. 154(b) by 0 days.

(21) Appl. No.: 13/998,703

(22) Filed: Nov. 26, 2013

(51) Int. Cl.
*A01H 5/12* (2006.01)

(52) U.S. Cl.
USPC ..... Plt./359

(58) Field of Classification Search
USPC ..... Plt./359
See application file for complete search history.

*Primary Examiner* — Susan McCormick Ewoldt
(74) *Attorney, Agent, or Firm* — C. A. Whealy

(57) ABSTRACT

A new and distinct cultivar of *Helichrysum* plant named 'Weshechrsisti', characterized by its compact and mounding plant habit; freely branching habit; dense and bushy growth habit; flexible branches; silvery green-colored leaves; and good garden performance.

1 Drawing Sheet

Botanical designation: *Helichrysum petiolare.*
Cultivar denomination: 'WESHECHRSISTI'.

BACKGROUND OF THE INVENTION

The present invention relates to a new and distinct cultivar of *Helichrysum* plant, botanically known as *Helichrysum petiolare* and hereinafter referred to by the name 'Weshechrsisti'.

The new *Helichrysum* plant is a naturally-occurring branch mutation of *Helichrysum petiolare* 'Ung Heli 04', not patented. The new *Helichrysum* plant was discovered and selected by the Inventor on a single plant of 'Ung Heli 04' in a controlled greenhouse environment in Worms, Germany in June, 2011.

Asexual reproduction of the new *Helichrysum* plant by vegetative cuttings in a controlled greenhouse environment in Worms, Germany since August, 2011 has shown that the unique features of this new *Helichrysum* plant are stable and reproduced true to type in successive generations.

SUMMARY OF THE INVENTION

Plants of the new *Helichrysum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Weshechrsisti'. These characteristics in combination distinguish 'Weshechrsisti' as a new and distinct *Helichrysum* plant:

1. Compact and mounding plant habit.
2. Freely branching habit, dense and bushy growth habit.
3. Flexible lateral branches.
4. Silvery green-colored leaves.
5. Good garden performance.

Plants of the new *Helichrysum* differ primarily from plants of the parent, 'Ung Heli 04', in leaf size and color as plants of the new *Helichrysum* have larger and more silvery-colored leaves than plants of 'Ung Heli 04'.

Plants of the new *Helichrysum* can also be compared to plants of the *Helichrysum* 'Nanum Silver', not patented. In side-by-side comparisons conducted in Worms, Germany, plants of the new *Helichrysum* differed primarily from plants of 'Nanum Silver' in the following characteristics:

1. Plants of the new *Helichrysum* were more freely branching and denser than and not as outwardly spreading as plants of 'Nanum Silver'.
2. Lateral branches of plants of the new *Helichrysum* were more flexible than lateral branches of plants of 'Nanum Silver'.
3. Plants of the new *Helichrysum* had smaller leaves than plants of 'Nanum Silver'.
4. Leaf apices of plants of the new *Helichrysum* were acute whereas leaf apices of plants of 'Nanum Silver' were obtuse.
5. Leaves of plants of the new *Helichrysum* were sessile whereas leaves of plants of 'Nanum Silver' were petioled.

BRIEF DESCRIPTION OF THE PHOTOGRAPH

The accompanying colored photograph illustrates the overall appearance of the new *Helichrysum* plant showing the colors as true as it is reasonably possible to obtain in colored reproductions of this type. Colors in the photograph may differ slightly from the color values cited in the detailed botanical description which accurately describe the colors of the new *Helichrysum* plant.

The photograph comprises a side perspective view of a typical plant of 'Weshechrsisti'.

DETAILED BOTANICAL DESCRIPTION

The aforementioned photograph and following observations, measurements and values describe plants grown during the summer in 12-cm containers a glass-covered greenhouse in Südlohn-Oeding, Germany and under cultural practices typical of commercial *Helichrysum* production. During the production of the plants, day temperatures ranged from 20° C. to 25° C., night temperatures ranged from 16° C. to 18° C. and light levels ranged from 3,000 to 50,000 lux. Plants were pinched twice and were five months old when the photograph and description were taken. In the following description, color references are made to The Royal Horticultural Society Colour Chart, 2001 Edition, except where general terms of ordinary dictionary significance are used.

Botanical classification: *Helichrysum petiolare* 'Weshechrsisti'.

Parentage: Naturally-occurring branch mutation of *Helichrysum petiolare* 'Ung Heli 04', not patented.

Propagation:

*Type.*—By vegetative cuttings.

*Time to initiate roots, summer.*—About two to three weeks at temperatures about 20° C.

*Time to initiate roots, winter.*—About three weeks at temperatures about 20° C.

*Time to produce a rooted young plant, summer.*—About four weeks at temperatures about 20° C.

*Time to produce a rooted young plant, winter.*—About five weeks at temperatures about 20° C.

*Root description.*—Thin to medium in thickness, fibrous; cream in color.

*Rooting habit.*—Freely branching; medium density to dense.

Plant description:

*Plant and growth habit.*—Compact and mounding plant habit; vigorous growth habit; freely branching habit with at least 15 lateral branches developing per plant; dense and bushy growth habit.

*Plant height.*—About 20 cm.

*Plant diameter or spread.*—About 70 cm.

*Lateral branches.*—Length: About 30 cm. Diameter: About 1 mm to 2 mm. Internode length: About 1 cm to 3 cm. Strength: Strong; flexible. Aspect: About 45° to 90° from vertical. Texture: Tomentose. Color: Close to 157B.

Leaf description:

*Arrangement.*—Alternate, simple; sessile.

*Length.*—About 1 cm to 1.5 cm.

*Width.*—About 5 mm.

*Shape.*—Elliptic.

*Apex.*—Acute.

*Base.*—Obtuse.

*Margin.*—Entire.

*Texture, upper and lower surfaces.*—Tomentose.

*Venation pattern.*—Pinnate.

*Color.*—Developing leaves, upper surface: Close to 190A. Developing leaves, lower surface: Close to 190D. Fully expanded leaves, upper surface: Close to 189C; venation, close to 189C. Fully expanded leaves, lower surface: Close to 190B; venation, close to 190B.

Inflorescence description: Inflorescence initiation and development have not been observed on plants of the new *Helichrysum*.

Disease & pest resistance: Plants of the new *Helichrysum* not been observed to be resistant to pathogens and pests common to *Helichrysum* plants.

Garden performance: Plants of the new *Helichrysum* have been observed to have good garden performance and tolerate rain, wind and temperatures ranging from about −2° C. to about 30° C.

It is claimed:

1. A new and distinct *Helichrysum* plant named 'Weshechrsisti' as illustrated and described.

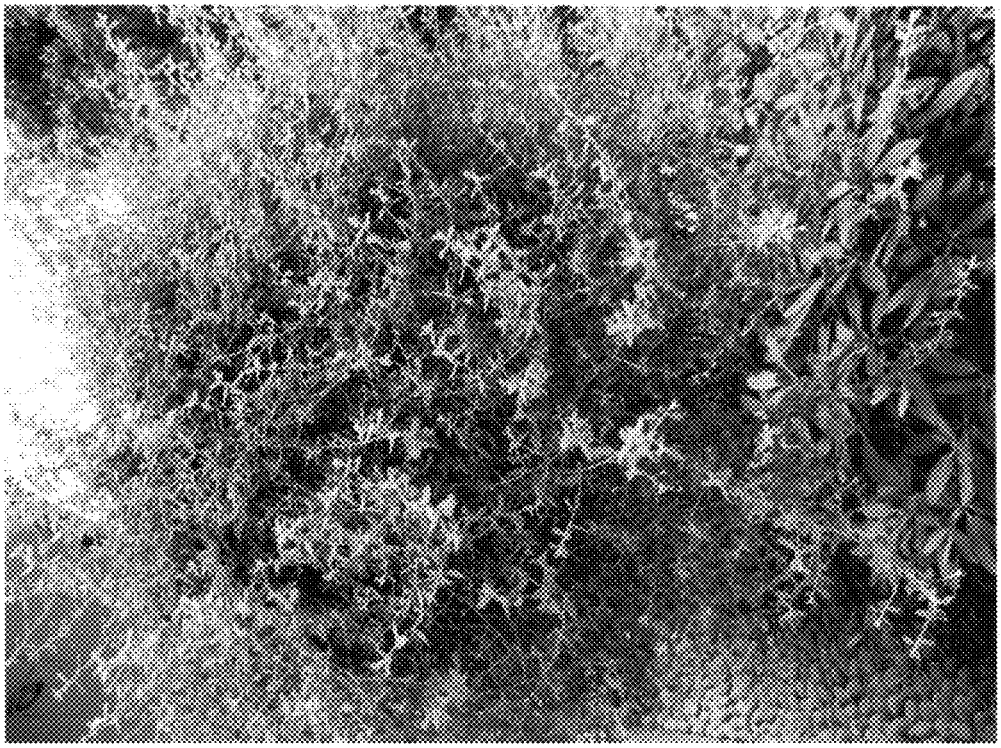

* * * * *